United States Patent
Kim

(10) Patent No.: US 6,414,590 B2
(45) Date of Patent: Jul. 2, 2002

(54) METHOD AND SYSTEM FOR MONITORING AN O2 SENSOR OF A VEHICLE

(75) Inventor: Yong-Sik Kim, Ansan (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 09/852,803

(22) Filed: May 11, 2001

(30) Foreign Application Priority Data

May 12, 2000 (KR) .......................... 2000-25356

(51) Int. Cl.$^7$ ................................ B60Q 1/00
(52) U.S. Cl. ............... 340/425.5; 340/439; 60/274; 123/489
(58) Field of Search .............. 340/425.5, 439; 73/23.32; 60/274, 276; 123/489, 674

(56) References Cited

U.S. PATENT DOCUMENTS

| | | | | |
|---|---|---|---|---|
| 4,848,300 A | * | 7/1989 | Samuel et al. | ............... 123/489 |
| 5,255,662 A | * | 10/1993 | Nakajima | ............... 123/674 |
| 5,440,877 A | * | 8/1995 | Kamura et al. | ............... 60/274 |
| 5,640,847 A | * | 6/1997 | Nakajima et al. | ............... 60/276 |
| 6,003,308 A | * | 12/1999 | Tsutsumi et al. | ............... 60/276 |

\* cited by examiner

*Primary Examiner*—Daniel J. Wu
*Assistant Examiner*—Phung Nguyen
(74) *Attorney, Agent, or Firm*—Birch, Stewart, Kolasch & Birch, LLP

(57) ABSTRACT

To more accurately detect malfunctioning of a front O2 sensor, after measuring a lean or a rich duration and calculating a reference duration related to the measured duration, and also by calculating a compensating value for the calculated reference duration, malfunction of the front O2 sensor is determined by comparing an accumulated value of the lean/rich durations and an accumulated value of the compensated reference durations.

5 Claims, 5 Drawing Sheets

METHOD AND SYSTEM FOR MONITORING AN O2 SENSOR OF A VEHICLE

CROSS-REFERENCE TO RELATED APPLICATION

This application claims priority of Korea patent Application No. 2000-25356, filed on May 12, 2000.

BACKGROUND OF THE INVENTION (a) Field of the Invention

The present invention relates to a method for monitoring an O2 sensor of a vehicle and a system thereof, and more particularly, to a method for detecting a malfunction of a front O2 sensor of a vehicle and warning of the malfunction, and a system thereof.

(b) Description of the Related Art

Exhaust gas of a vehicle, being understood as a main cause of atmospheric pollution, is under strict regulation along with smoke and noxious gases from factories, and in some leading nations, only vehicles that satisfy regulations are permitted to be sold.

Accordingly, recently produced vehicles are provided with a catalytic converter in their exhaust systems to accomplish more complete combustion. Furthermore, an engine is electronically controlled to reduce noxious exhaust gas and to improve mileage at the same time, an example of which is that fuel supply to the engine is controlled by an electronic control unit (written as ECU hereinafter) to maintain an appropriate Air/Fuel ratio based on signals from an oxygen sensor (written as O2 sensor hereinafter) disposed in front of the catalytic converter in the exhaust system.

Methods for detecting malfunctions of the front O2 sensor and methods for compensating values of variables used by the ECU to control fuel supply are investigated because if the front O2 sensor malfunctions, an appropriate Air/Fuel ratio cannot be maintained.

As an example of the methods, the exhaust system includes another O2 sensor (written as rear O2 sensor hereinafter) at the rear of the catalytic converter, and the exemplary method includes steps of:

measuring lean/rich durations of the rear O2 sensor at a predetermined driving condition, the condition being dependent on engine revolution speed and load;

calculating reference durations from a predetermined table recorded in the ECU;

accumulating the measured durations and the calculated reference durations respectively for a predetermined number of occurrences; and determining the front O2 sensor to be malfunctioning if the accumulated measured durations are greater than the accumulated reference durations.

FIG. 3 is a flowchart showing an O2 sensor monitoring method according to the prior art.

Referring to FIG. 3, an ECU determines whether a monitoring condition is satisfied at step S300. If the monitoring condition is satisfied, the ECU measures lean duration L and/or rich duration R of a front O2 sensor and calculates lean reference duration TL and/or rich reference duration TR on the basis of a predetermined reference table at step S310.

Each of the durations L and R and the reference durations TL and TR are accumulated at step S320 and the number of accumulations is counted at step S330. If the count is greater than a predetermined number at step S340, the ECU compares the accumulated duration L with the accumulated reference duration TL and/or the accumulated duration R with the accumulated reference duration TR at step S350. If one of the accumulated durations is greater than the corresponding accumulated reference duration, the ECU determines at step S360 that a front O2 sensor is malfunctioning.

The lean reference duration TL and the rich reference duration TR are calculated from predetermined functions of the engine state, of which independent variables to determine the engine state are engine speed and load, for example.

FIG. 4 is a set of graphs explaining a change of a fuel supply pattern according to a state of exhaust gas, especially when exhaust gas is determined to be lean.

The algorithm to change the fuel supply pattern is variously called P-Jump Delay or PTV/ATV, etc., depending on the manufacturer of the ECU, and hereinafter it is denoted as P-Jump Delay.

Because the Air/Fuel ratio of an engine is basically controlled on the basis of the signal from the front O2 sensor, a theoretical Air/Fuel ratio is not maintained in the case that the front O2 sensor malfunctions, for example through thermal breakdown. Therefore, a basic concept of the P-Jump Delay is that the ECU compensates for the malfunctioning of the front O2 sensor by feedback signals of a rear O2 sensor, the rear O2 sensor detecting the state of exhaust gas after the catalytic converter.

FIG. 4a is related to a normal state that a learned parameter (denoted as PJ_AD hereinafter) equals zero.

A dotted line shown in FIG. 4a indicates a target amount of fuel supply. In a normal state, the amount of fuel supply fluctuates around the dotted line as time passes, so that an average fuel supply over a period coincides with the dotted line. Therefore the target amount of fuel supply is achieved by injectors injecting fuel into an engine according to the fuel supply pattern of FIG. 4a.

An area above the dotted line, the area corresponding to an oversupply of fuel, is described as a positive area, and an area below the dotted line, the area corresponding to an insufficient supply of fuel, is described as a negative area.

A time division, in which fuel is injected constantly at a predetermined amount, is defined in each of the positive and negative areas. The time divisions are defined as delay time DLY_POS and DLY_NEG for the positive and negative areas respectively.

The delay times DLY_POS and DLY_NEG in a normal state are determined as base values POS and NEG respectively, the base values POS and NEG being predetermined values based on functions of the engine state, the functions having independent variables of, for example, engine speed and load.

Furthermore, a learning algorithm for compensating malfunctioning of the front O2 sensor is provided because if the front O2 sensor malfunctions, an appropriate Air/Fuel ratio is not maintained so that exhaust gas becomes rich or lean.

As a learning algorithm pointed out above, a learned parameter PJ_AD is learned on the basis of the history of detecting lean and rich states of exhaust gas from the rear O2 sensor, and the fuel supply pattern is modified on the basis of the learned parameter PJ_AD.

The fuel supply pattern is modified by modifying the delay time DLY_POS and/or DLY_NEG so that the amount of fuel-supplied is increased or decreased.

Normally, if the front O2 sensor malfunctions, the Air/Fuel ratio, basically controlled by the front O2 sensor, is controlled so that lean exhaust gas results.

To compensate the Air/Fuel ratio for the case exhaust gas is lean, the fuel supply pattern can be modified from the graph shown in FIG. 4a so that the delay time DLY_POS of the positive area is increased or the delay time DLY_NEG of the negative area is decreased by a value of the learned parameter PJ_AD.

Of the two ways of modifying, the latter is preferable because increasing the delay time DLY_POS causes a period of the fuel supply pattern to be unnecessarily increased, accordingly reducing frequency of control. Therefore, the fuel supply pattern is principally changed to one as shown in FIG. 4b if the exhaust gas is determined to be lean.

FIG. 4c is a graph of a fuel supply pattern relating to a state in which a learned parameter PJ_AD is greater than the base delay time NEG in the negative area.

If the learned parameter PJ_AD is greater than the base delay time NEG, insufficient fuel is supplied even if the delay time DLY_NEG is set to be 0. In such a case, as shown in FIG. 4c, the delay time DLY_POS must be increased by the value of the learned parameter PJ_AD minus the base time NEG, and the delay time DLY_NEG is set to be 0.

A method for changing the fuel supply pattern from FIGS. 4a to FIG. 4b or FIG. 4c is described hereinafter in further detail, referring to FIG. 5.

The ECU determines whether a signal from an O2 sensor satisfies a P-Jump Delay condition at step S400. The P-Jump Delay condition is preferably set to be such that the signal from the O2 sensor is changed from rich to lean.

If the signal from the O2 sensor satisfies the P-Jump Delay condition, a delay time DLY_NEG is calculated by subtracting the value of the learned parameter PJ_AD from the base delay time NEG at step S410.

If the delay time DLY_NEG is determined to be greater than 0 at step S420, the delay time DLY_POS of the positive area is set to be the base delay time POS at step S430. (See graph in FIG. 4b)

Accordingly, the fuel supply pattern is changed as shown if FIG. 4b and fuel is then supplied according to the changed fuel supply pattern at step S440.

If the delay time DLY_NEG is determined to be less than 0 at step S420, the delay time DLY_POS is increased by the value of the learned parameter PJ_AD minus the base time NEG, and the delay time DLY_NEG is set to be 0 at step S450.

Accordingly, the fuel supply pattern is changed as shown in FIG. 4c and fuel is then supplied according to the changed fuel supply pattern at step S440.

As described above, a method for monitoring malfunctions of an O2 sensor according to prior art considers effects of the learned parameter PJ_AD of the P-Jump Delay, but only in calculating the accumulation value TR of the rich reference duration TR (see step S320 in FIG. 3). Therefore, the effect of the learned parameter PJ_AD of the P-Jump Delay on the rich/lean duration is not fully considered in dealing with malfunctions of the O2 sensor so that a lack of accuracy occurs.

An example of the lack of accuracy is described in detail hereinafter.

The ECU must determine that the front O2 sensor is malfunctioning if the exhaust gas is repetitively determined to be excessively lean. If the exhaust gas is determined to be lean, the fuel supply pattern will be changed as shown in FIG. 4b or FIG. 4c by a learned parameter PJ_AD. As a result of learning, the next lean duration L is decreased from a previous one. Accordingly, when the step S320 in FIG. 3 is repeated, a lean duration L to be accumulated decreases as accumulation is repeated. However, a lean reference duration TL is not changed by a learned parameter PJ_AD of the P-Jump Delay so that if the lean duration occurs repeatedly at a specific engine state, the accumulated lean reference duration TL increases faster than the accumulated lean duration L, which results in the determining step S350 not detecting a malfunction of the O2 sensor.

SUMMARY OF THE INVENTION

The present invention has been made in an effort to improve accuracy of a method for monitoring malfunctions of an O2 sensor.

It is an objective of the present invention to provide a method and a system for monitoring the O2 sensor of a vehicle in which the method and the system consider a value of a learned parameter PJ_AD in accumulating a lean and rich reference duration TL and TR to improve accuracy of monitoring, and resultantly to reduce exhaust of noxious exhaust gas by noticing necessity of repair.

To achieve the above objective, the present invention provides a method for monitoring an O2 sensor of a vehicle, comprising:

measuring more than one duration among lean durations L and rich durations R according to a current engine state;

calculating more than one reference duration among lean reference durations TL and rich reference durations TR according to a current engine state, on the basis of a predetermined reference table;

calculating more than one correction value among correction values L_COR for lean reference duration and correction values R_COR for rich reference duration on the basis of a learned parameter PJ_AD of a P-Jump Delay;

calculating an accumulation value of durations selected among accumulation value L of the lean durations and accumulation value R of the rich durations, where an accumulation value relating to the measured duration is selected;

calculating an accumulation value of reference durations selected among accumulation value TL of the lean reference durations and accumulation value TR of the rich reference durations, where the accumulation value relating to the calculated correction value is selected; and, determining that an O2 sensor is malfunctioning if the calculated accumulation value of durations is greater than the calculated accumulation value of reference durations.

The step of determining malfunctions of the O2 sensor is preferably executed after the steps of measuring duration through calculating an accumulation value of reference durations are repeatedly executed for a predetermined number of times.

The calculating of the correction value entails calculating more than one correction value in such a way that:

the lean reference duration L_COR is calculated as 0 if the learned parameter PJ_AD of the P-Jump Delay is less than 0, as the base delay time NEG if the learned parameter PJ_AD is greater than the base delay time NEG, and as the value of the learned parameter PJ_AD if the learned parameter PJ_AD is in the range 0 to NEG; and the rich reference duration R_COR is calculated as 0 if the learned parameter PJ_AD of the P-Jump Delay is less than 0, as the value of the learned parameter PJ_AD minus the base delay time NEG if the learned parameter PJ_AD is greater than the base delay time NEG, and as 0 if the learned parameter PJ_AD is in the range 0 to NEG.

The calculating of the accumulation value of the reference durations is done using the following equations:

(TL)=(TL)+TL−L_COR (TR)=(TR)+TR+R_COR

To achieve the above objective, the present invention also provides a system for monitoring an O2 sensor of a vehicle, comprising:
- a front O2 sensor and a rear O2 sensor respectively disposed at a front and a rear of a catalytic converter;
- a warning means disposed in an interior of a vehicle for warning of a malfunction of the front O2 sensor; and
- an electronic control unit receiving signals from the O2 sensors, performing a method of claim 1 to determine malfunction of the front O2 sensor, and operating the warning means if the front O2 sensor is determined to be malfunctioning.

BRIEF DESCRIPTION OF THE DRAWINGS

The accompanying drawings, which are incorporated in and constitute a part of the specification, illustrate an embodiment of the invention, and, together with the description, serve to explain the principles of the invention:

FIG. 4 is a set of graphs explaining change of fuel supply pattern when exhaust gas is determined to be lean, wherein

DETAILED DESCRIPTION OF THE PREFERRED EMBODIMENTS

A preferred embodiment of the present invention will hereinafter be described in detail with reference to the accompanying drawings.

Figure 1:
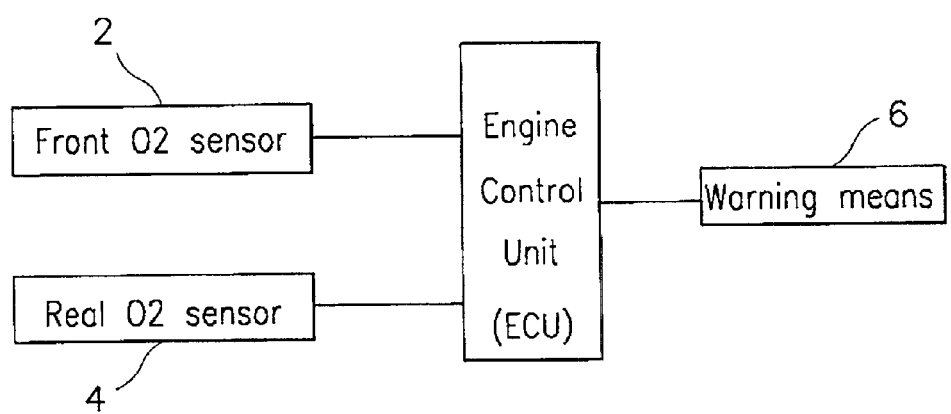
FIG. 1 is a block diagram of an O2 sensor monitoring system according to a preferred embodiment of the present invention.

FIG. 1 is a block diagram of an O2 sensor monitoring system according to a preferred embodiment of the present invention.

Referring to FIG. 1, a front O2 sensor 2 and a rear O2 sensor 4 are disposed respectively at a front and a rear of a catalytic converter in an exhaust system of an automotive engine. Furthermore, an electronic control unit (written as ECU hereinafter) and a warning means 6 disposed at a predetermined position in an interior of a vehicle are provided so that the ECU determines whether the front O2 sensor 2 is malfunctioning based on inputted signals from the O2 sensors 2 and 4, and operates the warning means 6 when the front O2 sensor is determined to be malfunctioning.

Air/Fuel ratio of an engine is controlled basically on the basis of the signal from the front O2 sensor 2. If the Air/Fuel ratio is changed to be lean because of malfunctioning of the front O2 sensor, for example through thermal breakdown, the rear O2 sensor 4 detects lean exhaust gas so that the ECU modifies the fuel supply pattern to maintain an appropriate Air/Fuel ratio, and warns of the malfunctioning by operating the warning means 6.

Figure 2:
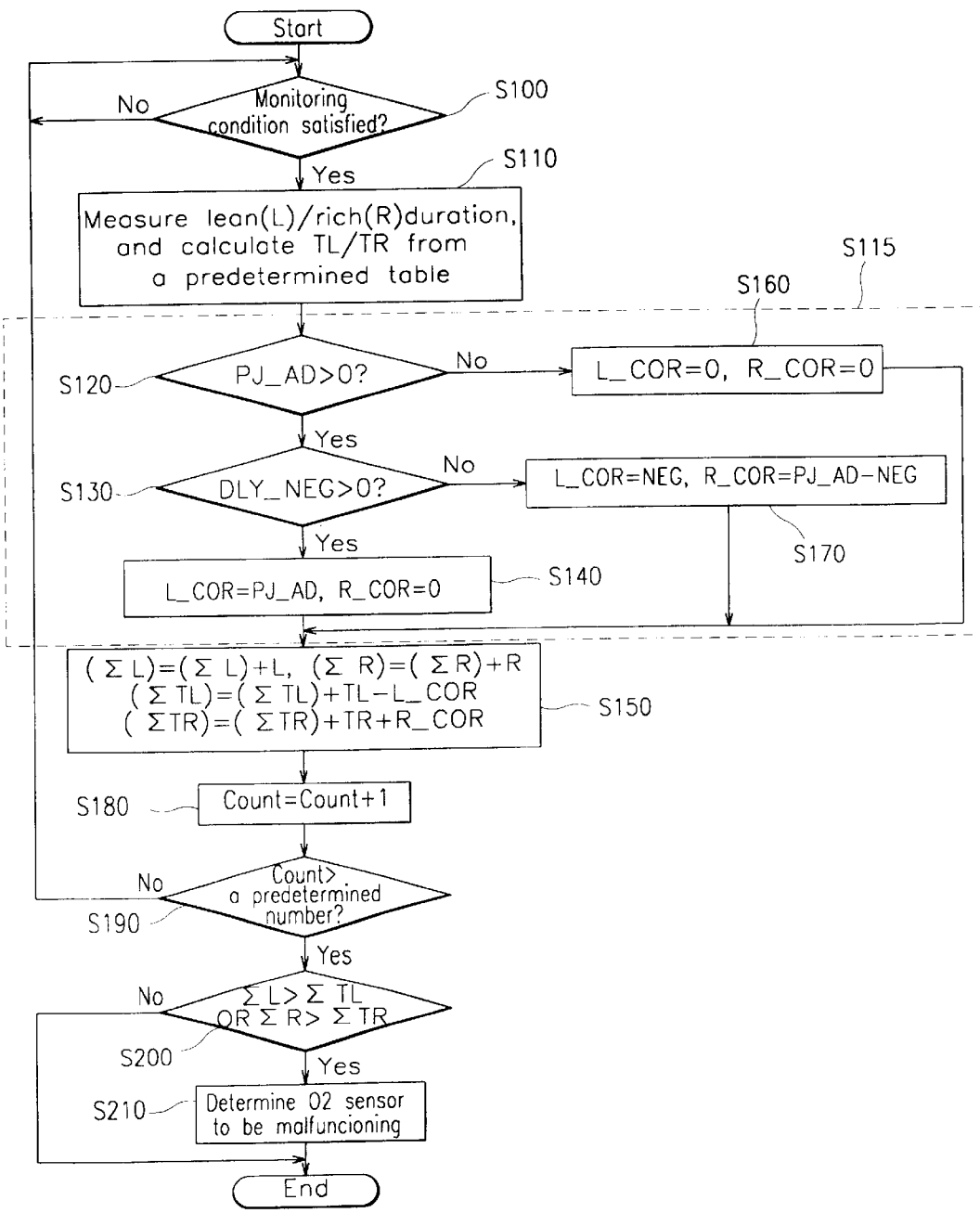
FIG. 2 is a flowchart showing an O2 sensor monitoring method according to a preferred embodiment of the present invention.
Figure 3:
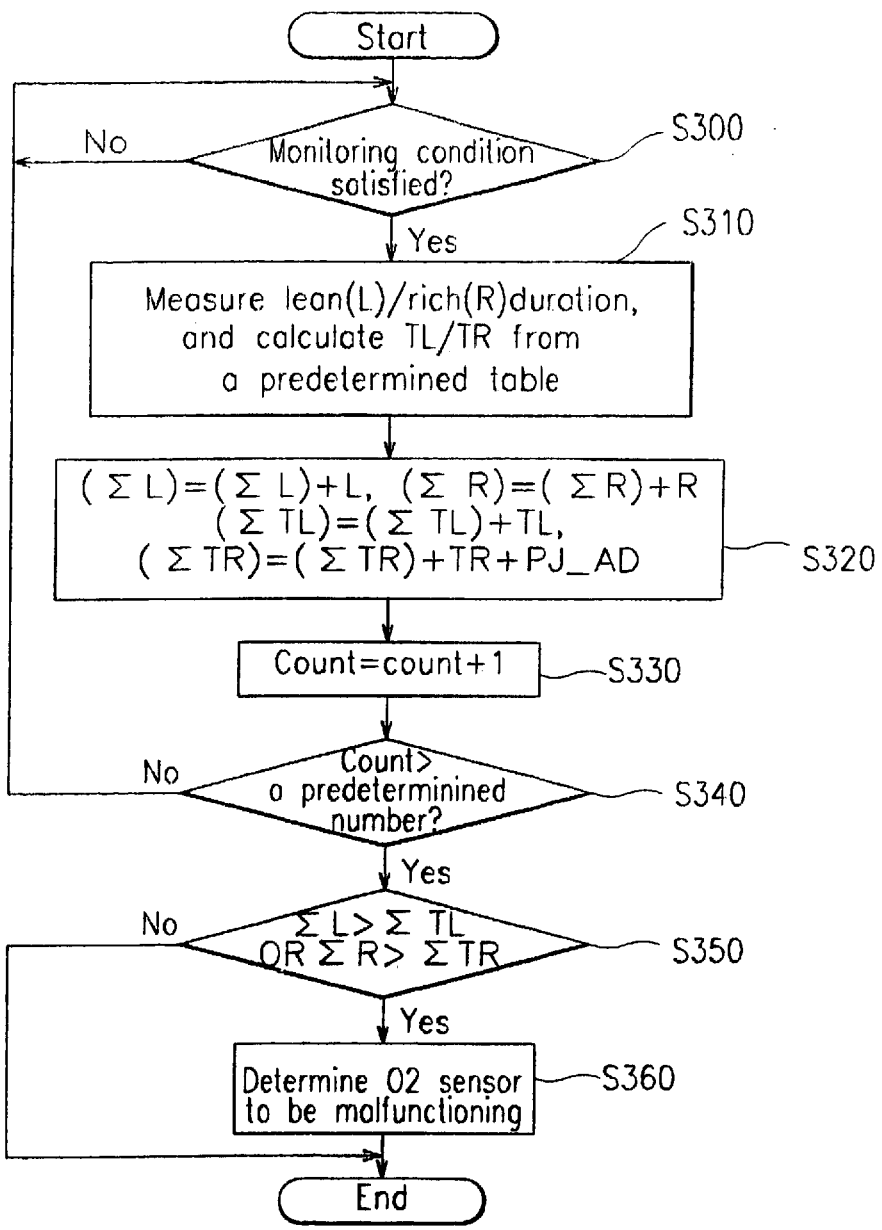
FIG. 3 is a flowchart showing an O2 sensor monitoring method according to prior art.
Figure 4A:
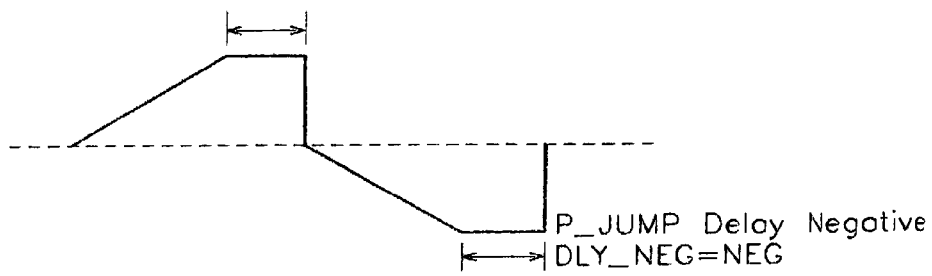
FIG. 4a is related to a normal state that a learned parameter PJ_AD of P-Jump Delay equals to zero.
Figure 4B:
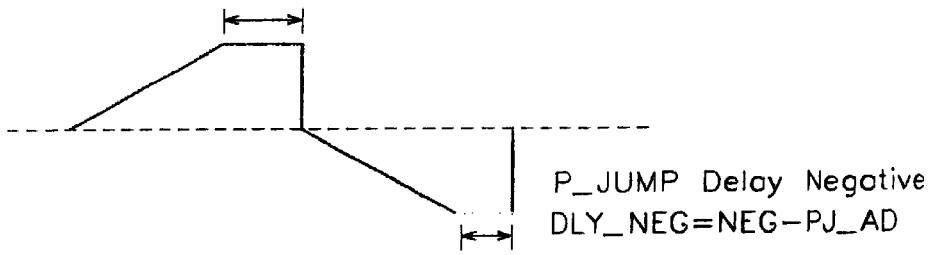
FIG. 4b is related to a state that a learned parameter PJ_AD is less than a base delay time NEG in a negative area.
Figure 4C:
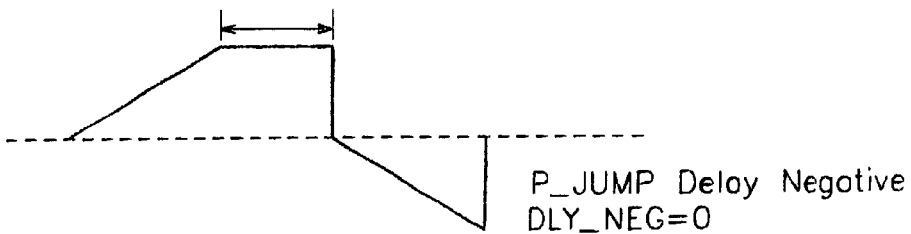
FIG. 4c is related to a state that a learned parameter PJ_AD is greater than the base delay time NEG.
Figure 5:
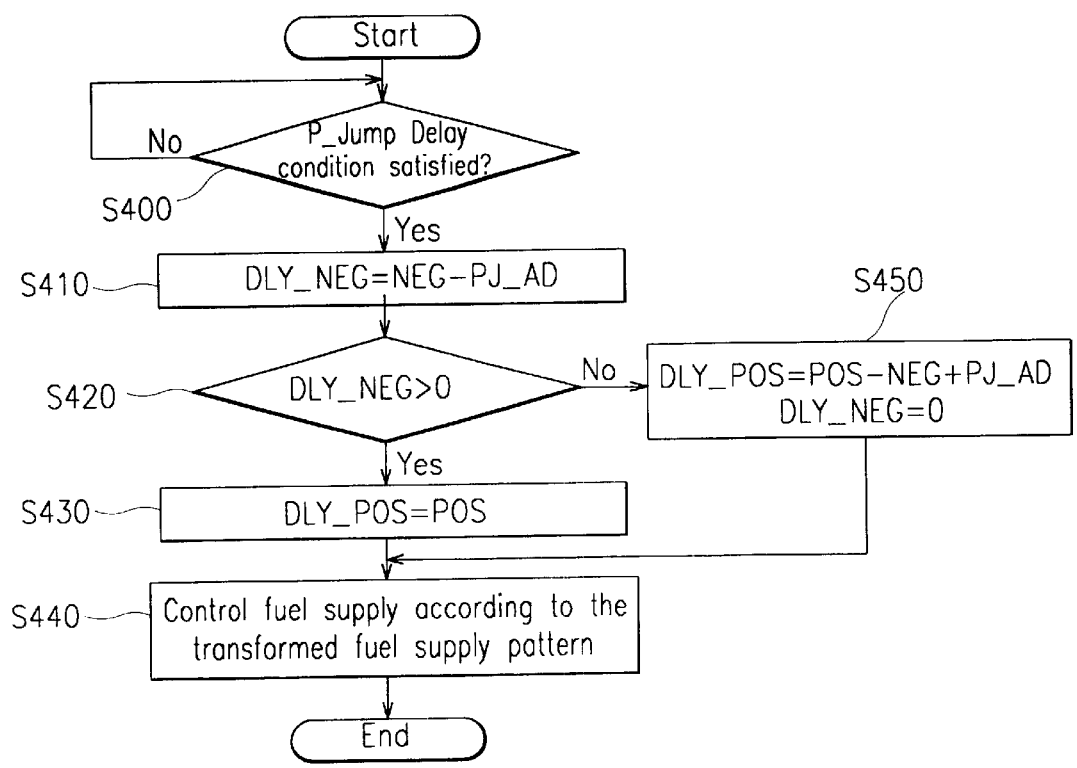
FIG. 5 is a flowchart showing a method for changing the fuel supply pattern.

FIG. 2 is a flowchart showing an O2 sensor monitoring method according to a preferred embodiment of the present invention.

Referring to FIG. 2, at step S100 the ECU determines whether a state of a vehicle satisfies a monitoring condition.

The monitoring condition is predetermined to be any condition appropriate for monitoring, and preferably predetermined to be a condition in which the catalytic converter is activated and vehicle parameters are in predetermined ranges, the vehicle parameters being, for example, temperature of engine, vehicle speed, engine speed and air induction ratio.

The monitoring condition may vary in accordance with types of vehicle and engine. A more specific example of the monitoring condition is that the vehicle speed be in a 5–72 km/h range, engine speed be in an 800–2700 rpm range and the air induction ratio be between 160–260 mg/TDC where the given ranges are set in accordance with a normal operating state of an engine.

If the monitoring condition is satisfied, the ECU measures a lean duration L or a rich duration R, and calculates a lean reference duration TL or a rich reference duration TR from a predetermined reference table at step S110.

At the above step S10, the recent duration of lean state is measured if the state of an engine is changed from lean to rich, and the recent duration of rich state is measured if the state of the engine is changed from rich to lean. In the same way, one of the reference durations TL and TR is calculated on the basis of engine state.

Thereafter, the ECU calculates a correction value L_COR or R_COR to modify the reference duration TL or TR on the basis of the learned parameter PJ_AD at step S115. The correction value to calculate is chosen on the basis of current engine state.

The lean reference duration L_COR is calculated as 0 if the learned parameter PJ_AD of the P-Jump Delay is less than 0, as the base delay time NEG if the learned parameter PJ_AD is greater than the base delay time NEG, and as the value of the learned parameter PJ_AD if the learned parameter PJ_AD is in the range of 0 to NEG.

The rich reference duration R_COR is calculated as 0 if the learned parameter PJ_AD of the P-Jump Delay is less than 0, as the value of the learned parameter PJ_AD minus the base delay time NEG if the learned parameter PJ_AD is greater than the base delay time NEG, and as 0 if the learned parameter PJ_AD is in the range of 0 to NEG.

In further detail, the ECU, determining whether the learned parameter PJ_AD of the P-Jump Delay is greater than 0 at step S120, set the lean and rich correction valves L_COR and R_COR to 0 if the parameter PJ_AD is not greater than 0 at step S160.

If the parameter PJ_AD is greater than 0 at step S120, the ECU further determines whether the delay time DLY_NEG in the negative area is greater than 0 at step S130, the delay time DLY_NEG being already modified by the learned parameter PJ_AD.

If the delay time DLY_NEG is greater than 0 at step S130, the correction values L_COR and R_COR of lean and rich reference duration are set to the learned parameter PJ_AD and 0 respectively at step S140.

If the delay time DLY_NEG is not greater than 0 at step S130, the correction value L_COR of lean reference duration is set to the base delay time NEG, and the correction value R_COR of rich reference duration is set to a value of the learned parameter PJ_AD minus the base delay time NEG at step S170.

Having calculated correction value L_COR or R_COR corresponding to current engine state, the ECU calculates accumulation values L and TL of a lean state, or R and TL of a rich state corresponding to a current engine state at S150.

Each value is accumulated according to the following equations:

$$(L)=(L)+L,$$

$$(R)=(R)+R,$$

$$(TL)=(TL)+TL-L\_COR, \text{ and}$$

$$(TR)=(TR)+TR+R\_COR.$$

Steps from step S110 for measuring duration and for calculating reference duration through step S150 for calculating accumulation values are repeated by a predetermined number of repetitions (see S180 and S190).

By comparing thereafter the accumulated value of the measured durations and the accumulated value of the modified reference durations at step S200, the ECU determines that the front O2 sensor is malfunctioning if the accumulated value of the measured durations is greater than that of the modified reference durations at step S210.

The lean reference durations TL and the rich reference durations TR are calculated from a predetermined reference table based on such functions as engine state, of which independent variables to determine the engine state are, for example, engine speed and load.

As described above, this invention accumulates the reference durations TL and TR as being modified by a learned parameter PJ_AD of a P-Jump Delay to effect learning, in which the parameter PJ_AD affect the durations L and R, so that accuracy is improved.

Therefore according to this invention, accuracy in monitoring malfunctions of a front O2 sensor is improved because the learned parameter PJ_AD is also considered in accumulating the reference duration.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A method for monitoring an O2 sensor of a vehicle, comprising:

measuring more than one duration among lean durations L and rich durations R according to a current engine state;

calculating more than one reference duration among lean reference durations TL and rich reference durations TR according to a current engine state, on the basis of a predetermined reference table;

calculating more than one correction value among correction values L_COR for lean reference duration and correction values R_COR for rich reference duration on the basis of a learned parameter PJ_AD of a P-Jump Delay;

calculating an accumulation value of durations selected among accumulation value L of the lean durations and accumulation value R of the rich durations, where an accumulation value relating to the measured duration is selected;

calculating an accumulation value of reference durations selected among accumulation value TL of the lean reference durations and accumulation value TR of the rich reference durations, where the accumulation value relating to the calculated correction value is selected; and, determining that an O2 sensor is malfunctioning if the calculated accumulation value of durations is greater than the calculated accumulation value of reference durations.

2. A method of claim 1, wherein the step of determining malfunctions of the O2 sensor is executed after the steps of measuring duration through calculating an accumulation value of reference durations are repeatedly executed for a predetermined number of times.

3. A method of claim 2 wherein the calculating correction value calculates more than one correction value in a way that:

the lean reference duration L_COR is calculated as 0 if the learned parameter PJ_AD of the P-Jump Delay is less than 0, as the base delay time NEG if the learned parameter PJ_AD is greater than the base delay time NEG, and as the value of the learned parameter PJ_AD if the learned parameter PJ_AD is in the range 0 to NEG; and the rich reference duration R COR is calculated as 0 if the learned parameter PJ_AD of the P-Jump Delay is less than 0, as the value of the learned parameter PJ_AD minus the base delay time NEG if the learned parameter PJ_AD is greater than the base delay time NEG, and as 0 if the learned parameter PJ_AD is in the range 0 to NEG.

4. A method of claim 2, wherein calculating the accumulation value of the reference durations is done using the following equations:

$$(TL)=(TL)+TL-L\_COR$$

$$(TR)=(TR)+TR+R\_COR.$$

5. A system for monitoring an O2 sensor of a vehicle, comprising:

a front O2 sensor and a rear O2 sensor respectively disposed at a front and a rear of a catalytic converter;

a warning means disposed in an interior of a vehicle for warning of a malfunction of the front O2 sensor; and an electronic control unit receiving signals from the O2 sensors, performing a method of claim 1 to determine malfunction of the front O2 sensor, and operating the warning means if the front O2 sensor is determined to be malfunctioning.

* * * * *